United States Patent [19]

Bartholomay

[11] Patent Number: 4,587,858
[45] Date of Patent: May 13, 1986

[54] CROSSCUT SAMPLER WITH AUGER CLEAN OUT

[75] Inventor: Donald O. Bartholomay, St. Louis Park, Minn.

[73] Assignee: Gustafson, Inc., Dallas, Tex.

[21] Appl. No.: 695,620

[22] Filed: Jan. 28, 1985

[51] Int. Cl.[4] .............................................. G01N 1/20
[52] U.S. Cl. ............................. 73/863.53; 73/863.54
[58] Field of Search ........... 73/863.53, 863.54, 863.55, 73/863.56

[56] References Cited

U.S. PATENT DOCUMENTS

| | | |
|---|---|---|
| 2,313,715 | 3/1943 | Andlauer . |
| 2,738,679 | 3/1956 | Stenkowski . |
| 2,795,141 | 6/1957 | Pate . |
| 3,060,746 | 10/1962 | Gompper . |
| 3,217,547 | 11/1965 | Cordell et al. . |
| 3,383,924 | 5/1968 | Cordell . |

FOREIGN PATENT DOCUMENTS 903119  8/1962  United Kingdom ............. 73/863.55

*Primary Examiner*—Stewart J. Levy
*Assistant Examiner*—Tom Noland
*Attorney, Agent, or Firm*—Palmatier & Sjoquist

[57] ABSTRACT

A crosscut sampler with an auger cleanout comprising a housing insertable into a gravity feed flow duct containing a flowing stream of dry material, a pelican with a receiving slot movably mounted within the housing for transversely transversing the stream to collect a sample, and an auger on the bottom of the pelican for withdrawing all of the sample from the pelican.

8 Claims, 3 Drawing Figures

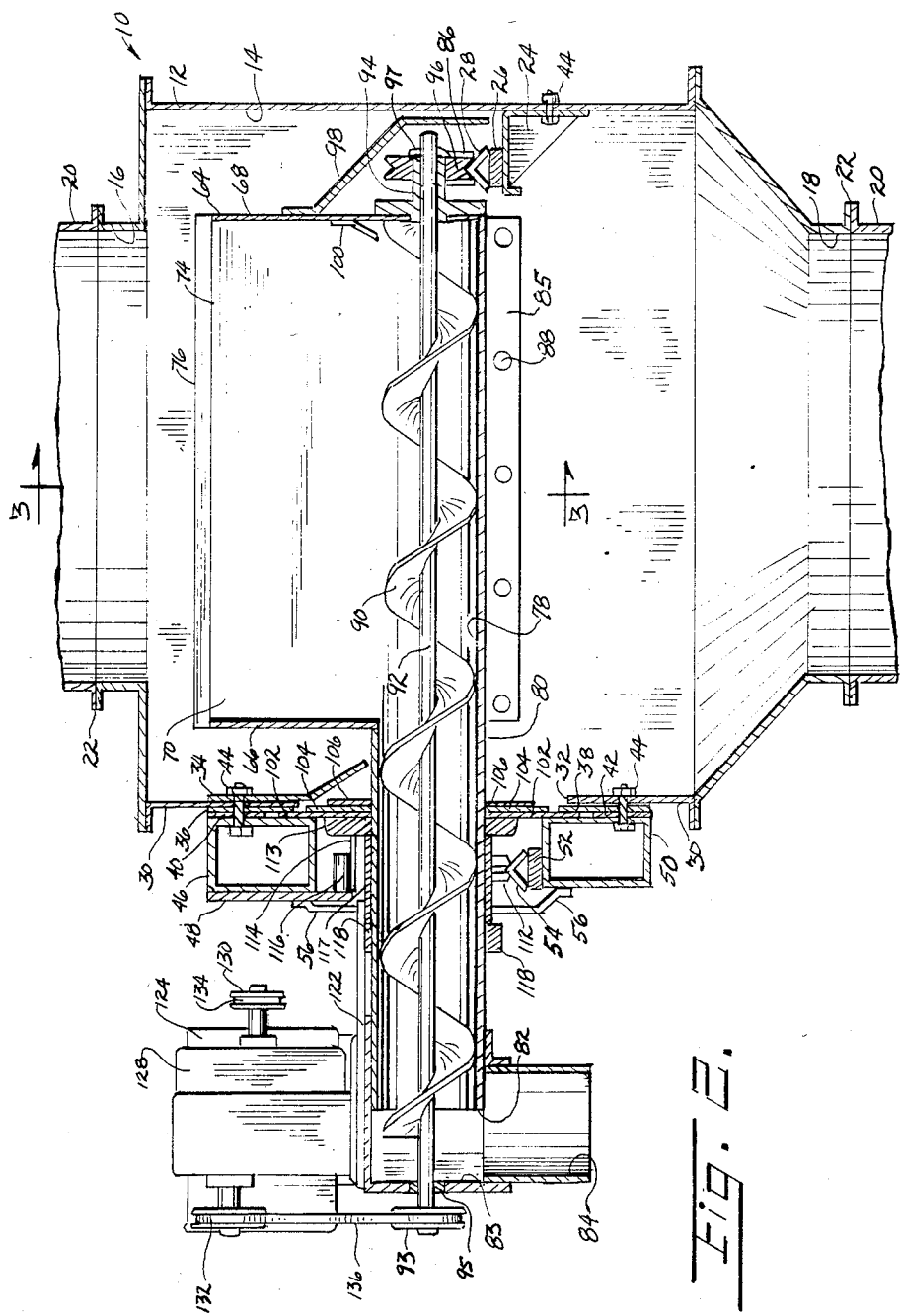

CROSSCUT SAMPLER WITH AUGER CLEAN OUT

BACKGROUND OF THE INVENTION

The invention relates to a dry material sampling apparatus and more particularly to a crosscut sampler with auger cleanout insertable into a gravity feed flow duct for obtaining a representative sample of a downwardly flowing stream of dry material within the duct.

Granular materials, such as grains, pellets or granules, and powdery materials, such as portland cement, are often conveyed in gravity feed flow ducts. Such dry materials are intially loaded into elevated reservoirs or bins. Ducts are connected to the bottoms of the bins. Gravity may then be utilized as the moving force to disburse the materials into the ducts for sorting, storage elsewhere or usage.

Obtaining a representative sample of a large quantity of dry material is difficult. Dry materials do not have the uniform physical and qualitative consistencies of liquids. Additionally, finer granular materials have a tendency to more readily settle below larger granular materials thereby creating striations within a material of differently sized particles. It is generally accepted that the most representative sample of a dry material may be obtained while the material is being conveyed and flowing within a duct. Such samples may be then analyzed for physical and qualitative characteristics to be used in characterizing the material flowing within the duct at the time of sampling.

In the past, various samplers have attempted to take representative samples from a gravitationally flowing stream of dry materials. U.S. Pat. No. 2,313,715, issued to Andlauer on Mar. 16, 1943 shows a feed volume meter and sampler where the feed is diverted over a corrugated drum, by a swingable gate and into a test box. U.S. Pat. No. 2,738,679, issued to Senkowski on Mar. 20, 1956 discloses a solid sample cutter with an inclined bottom for gravitationally directing the collected sample into a bin. U.S. Pat. No. 2,795,141, issued to Pate on June 11, 1957 reveals a sampler cutter in a sloping material delivery chute which delivers samples into a hopper. Automatic sampler models G/A and G/E, manufactured by Gustafson, Inc. of Dallas, Tex., are crosscut samplers with pelicans insertable in gravity feed flow ducts. The pelicans have inclined bottoms for diverting the samples thereout. The above samplers require sizable vertical spacing or head room for gravity to effectively deliver the material samples therefrom and may not work with both granular powdery materials.

Augers have been used to withdraw sample material from bulk materials as shown in U.S. Pat. No. 3,060,746, issued to Gompper on Oct. 30, 1962, U.S. Pat. No. 3,217,547, issued to Cordell et al. on Nov. 16, 1965 and U.S. Pat. No. 3,383,924, issued to Cordell on May 21, 1968 teach of sampling devices for pressurized conveyors using augers to deliver material samples. These samplers have their augers within tubes having slots for a material sample to enter the tube. Such tubes are stationary or have restricted linear movement. Therefore, they do not give the most accurate sample of a material having any varing characteristics.

There is a need to provide a crosscut sampler that accurately provides representative crosscut samples from a gravity feed flow duct, requires mimimal vertical space and operates with a wide range of granular to powdery materials.

SUMMARY OF THE INVENTION

In the present invention, the sampler has a housing with top and bottom openings to communicate with a flow duct and a side wall with an elongate generally horizontal hole. The housing encloses a pelican which transversely traverses through the stream of flowing material. The pelican has a top wall with a receiving slot, a bottom and a front wall. The front wall has an auger tube adjacent the bottom which extends through the elongate slot of the housing with a discharge outlet at its end. The pelican and housing have a cooperating support and guide structure to accommodate movement of the pelican. A slide panel is transversely affixed about the auger tube adjacent the side wall of the housing overlapping the elongate hole. A drive means is connected to the pelican for moving the pelican along the support structure. An auger is within the pelican on the bottom and extends through the auger tube to the discharge outlet. A motor rotates the auger.

The housing provides a chamber enclosing the pelican and containing the material. The top and bottom openings are for splicing the housing into a gravity feed flow duct in a sealed arrangement. The elongate hole permits for withdrawal of a material sample from the housing. The receiving slot permits a sample of the material to enter the pelican and be collected on its bottom as the pelican transversely moves through and beyond the stream of the material. The auger tube in the front wall with its discharge outlet provides an extension of the pelican which protudes through the elongate hole outside the housing from where the sample may be withdrawn. The support and guide structure is for movably mounting the pelican within the housing. The slide panel about the auger tube is for sliding engagement with the side wall of the housing. The slide panel overlaps the elongate hole to prevent exit of the material from the housing through the elongate hole except through the discharge outlet. The drive means moves the pelican along the support structure passing the receiving slot through and beyond the stream to collect a sample. The auger and its motor withdraws and cleans all of the sample material from the pelican's bottom to the outside of the housing.

The invention advantageously provides a crosscut sampler that accurately provides representative crosscut material samples from a gravity feed flow duct. The entire sample is cleaned out of the sampler which operates with a wide range of granular to powdery materials. Minimal vertical spacing or head room is required that allows positioning of the crosscut sampler in places heretofore not known.

BRIEF DESCRIPTION OF THE DRAWINGS

FIG. 2 is a cross sectional view along lines 2—2 of FIG. 1; and

DETAILED DESCRIPTION

Figure 1:
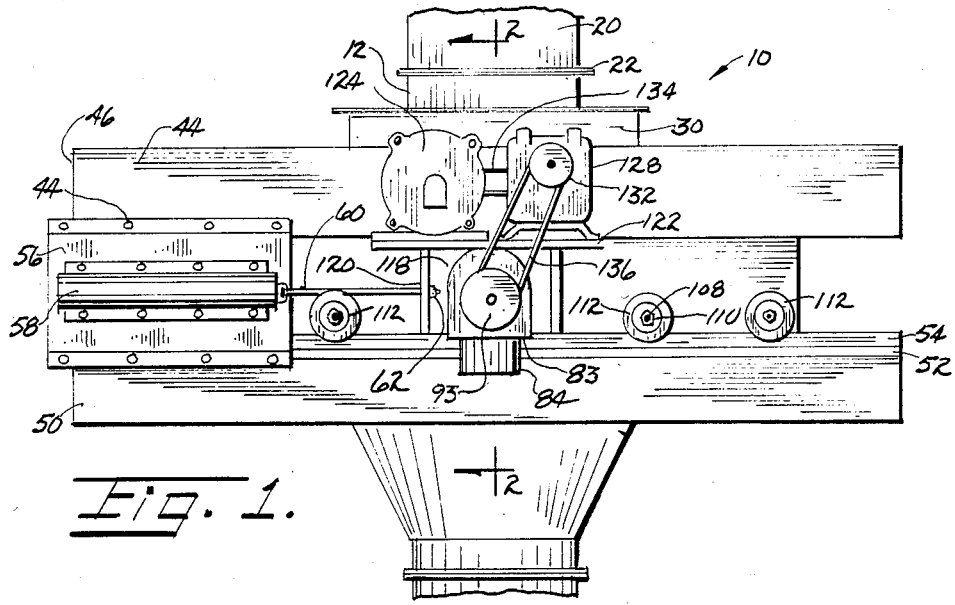
FIG. 1 is a front elevational view of the crosscut sampler with auger cleanout spliced into a vertical gravity feed flow duct.

Referring to FIGS. 1 and 2, the crosscut sampler with auger cleanout is generally indicated by numeral 10. Crosscut sampler 10 has a housing 12 with top opening or spout 16 and bottom opening 18. Housing 12 is spliced into a vertical gravity feed flow duct 20 at openings 16 and 18 suitably fastened by cooperating flanges 22. An elongate support bracket 24 is on the inside of side wall 14 of housing 12 and is suitably horizontally mounted by bolts 44. Bracket 24 has spacer 26 which supports track 28.

In opposing side wall 30 of housing 12 is an elongate horizontal hole 32 opposite track 28. Above elongate hole 32, deflector 34, wear plate 36, channel mounting plate 40, and upper box channel 46 are all suitably affixed to side wall 30 by bolts 44 or welding. An auxiliary frame plate 48 is also affixed to the front of upper box chanel 46. Below elongate hole 32, wear plate 38, channel mounting plate 42 and lower box channel 50 are likewise suitably affixed to side wall 30 by bolts 44 or welding. Lower box channel 50 has spacer 52 on its top which supports track 54. Track 54 is generally parallel to track 28. Drive mounting plate 56 is attached to auxiliary frame plate 48 and lower box channel 50 suitably by bolts or other fasteners. Air cylinder 58 is mounted on mounting plate 54 by fasteners and has an actuating shaft 60.

Figure 3:
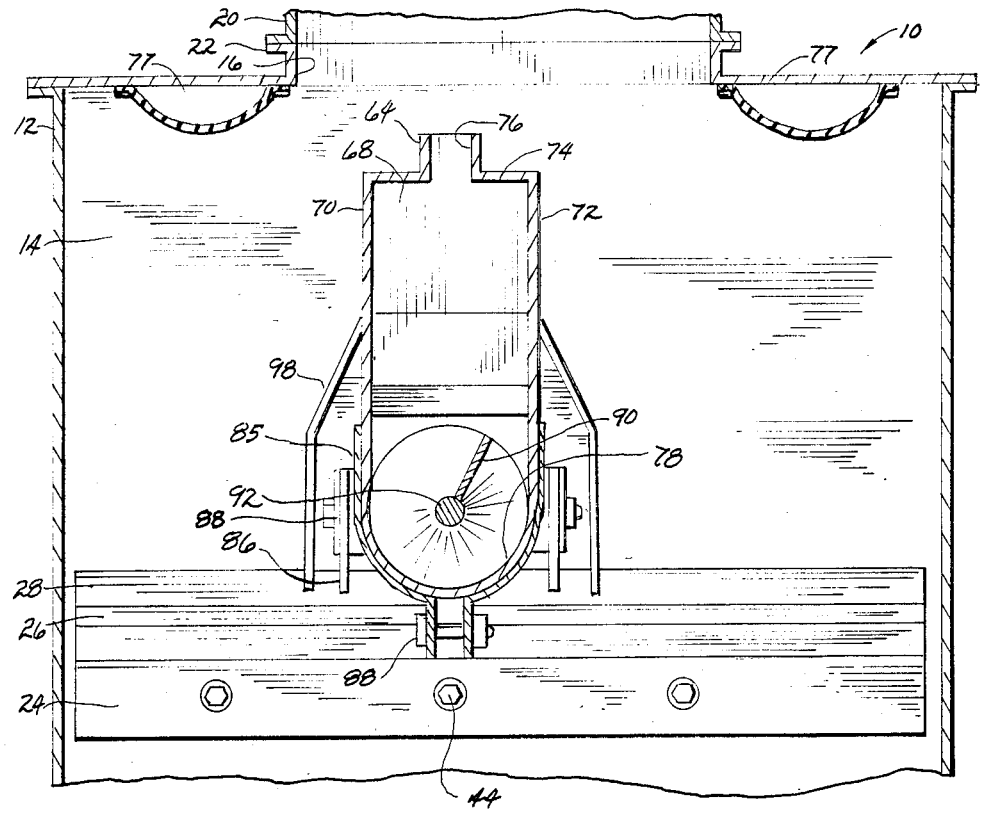
FIG. 3 is a cross sectional view along lines 3—3 of FIG. 2.

As shown in FIGS. 2 and 3, pelican 64 is within housing 12. Pelican 64 has front 66, back 68 and side 70, 72 walls. Pelican 64 also has top wall 74 with a receiving slot 76 and a preferably horizontal bottom 78 that is concave or semi-circular in cross section. Dust seals 77 are above the cover receiving slot 76 when pelican 64 is at rest outside the flowing stream of material. Auger tube 80, which communicates with the inside of pelican 64, extends from front wall 66 adjacent bottom 78 through elongate hole 32 of housing 12. An opening 82 is at the end of auger tube 80. Discharge elbow 83 is fitted over opening 82 at the end of auger tube 80 and suitably held there by fasteners or welding. Discharge elbow 83 has a discharge outlet 84 which communicates with opening 82. Stiffener 85 with track wipers 86 is attached about the outside of the bottom 78 suitably by bolts 88. Because bottom 78 is preferably horizontal, housing 12 requires only a minimal amount of vertical spacing to movably support and enclose pelican 64 as it traversely traverses through the stream of material.

Auger 90 on central shaft 92 lies on bottom 78 and extends through auger tube 80 to opening 82. Shaft 92 extends further through a bushing and bearing assembly 95 in discharge elbow 83 and has a drive pulley 93 at its end. The other end of shaft 92 extends through another bushing and bearing assembly 94 located in back wall 68. Outside back wall 68, assembly 94 has a free rolling roller 96 which rides on track 28 and is held there by retainer 97 on shaft 92. Shield 98 is suitably attached to the outside of back wall 68 and covers assembly 94 and roller 96. Deflector 100 is attached to the inside of back wall 68 above the end of aguer 90.

Slide panel 102 is suitably transversely welded about auger tube 80 adjacent or where auger tube 80 extends through elongate hole 32. Stiffening plates 104 and 106 about auger tube 80 are adjacent, behind and suitably bolted to panel 102. The front of slide panel 102 has four threaded stub shafts 108 each with a bearing and a nut or fastener 110 for supporting and retaining a free rolling roller 112 which rides on track 54 (FIG. 1). Mounting plate 113 is suitably bolted to the front of slide panel 102. Mounting plate 113 has a bracket 114 with a shaft and bearing assembly which supports a free rolling roller 116. Roller 116 rides on a portion of the back side of auxiliary frame plate 48. Drive support plate 118 about auger tube 80 adjacent drive mounting plate 56 is suitable affixed to auger tube 80, such as by roll pins, and welded to mounting tube 117 which is about auger tube 80. Flange 120 of support plate 118 receives the threaded end of shaft 60 which is suitably held there by nut or fastener 62.

Referring again to FIGS. 1 and 2, mounting tube 117, drive support plate 118 and discharge elbow 83 are suitably welded or fastened to and support a mounting plate 122. Motor 124 with pulley 126 and gear reducer 128 with pulleys 130 and 132 are mounted on mounting plate 122. Power transmissions are formed by belt 134 wrapped about pulleys 126 and 130 and belt 136 about pulleys 132 and 93.

Once housing 12 is spliced into gravity feed flow duct 20, dry material may freely pass through housing 12 while pelican 64 is out of the stream of material in rest position with its receiving slot 76 covered by one of either dust seals 77. Upper and lower box channels 46 and 50, which are affixed to housing 12, provide rigid mounting surfaces for track 54, auxiliary frame plate 48 and drive mounting plate 56. Track 28 is also securely affixed to housing 12. Pelican 64 has rollers 96, 112 and 116 connected thereto which in turn ride on tracks 28 and 54 and auxiliary frame plate 48 respectively thereby movably mounting pelican 64. This mounting arrangement allows for linear movement of pelican 64 so that receiving slot 76 may traversely traverse through the entire stream of flowing material in housing 12. Air cylinder 58, which is securely mounted on drive mounting plate 56, has its actuating shaft 60 secured to flange 120 of drive support plate 118 by fastener 62 so that air cylinder 58 may move pelican 64, including auger tube 80, in a linear reciprocating manner.

Elongate hole 32 provides an opening in the housing for auger tube 80 from which the sample material is withdrawn. Hole 32 is preferably elongate and horizontal to accommodate the linear reciprocating movement of auger tube 80 as it extends through elongate hole 32.

Deflector 34 deflects falling dry material in housing 12 from elongate hole 32 and slide panel 102. Similarly, shield 98 protects roller 96 and assembly 94 from falling dry material while track wipers 89 clean track 28.

Slide panel 102 about auger tube 80 is suitably bolted to seal and prevent material from passing therebetween. Slide panel 102 is adjacent side wall 30 and of sufficient length so that it continuously overlaps elongate hole 32 whatever the position of pelican 64. Stiffening plates 104 and 106 add rigidity to slide panel 102 as pelican 64 moves and collects a material sample. Wear plates 36 and 38, affixed to side wall 30, provide a surface upon which slide panel 102 bears as its moves in the space defined by wear plates 36 and 38, channel mounting plates 40 and 42, and box channels 46 and 50. This structure provides a sealing arrangement so that dry material cannot exit housing through elongate hole 32 as auger tube 80 reciprocates in linear fashion.

Pelican 64 is enclosed by walls 66, 68, 70 and 72 to hold the sample material entering the pelican 64 through receiving slot 76. Stiffener 85 adds rigidity to pelican 64 as it collects the sample from the impacting stream of material which pelican 64 must pass through. The bottom 78 of pelican 64 is concave to provide maximum contact with auger 90 thereby assuring that all the material sample collected on bottom 78 will be cleaned out of pelican 64. Auger tube 80 provides an extension of bottom 78 that extends through elongate hole 32 of housing 12 in a sealed arrangement from where the collected sample may be extracted or withdrawn outside housing 12. Bushing and bearing assemblies 94 and 95 secure central shaft 92 in pelican 64 as it rotates auger 90 against bottom 78. Auger 90 has a diameter slightly less than bottom 78 so as to closely fit against bottom 78. Deflector 100 diverts the falling sample material within pelican 64 away from the withdrawing end of auger 90 to prevent any material build-up or caking that could otherwise occur there. As auger 90 turns, it cleans out bottom 78 withdrawing all the sample material collected out opening 82 to discharge elbow 83 and discharge outlet 84 which deflect the extracted sample downward for collection.

A power transmission to rotate auger 90 is created by belt 136 about central shaft's 92 pulley 93 and gear reducer's 128 pulley 132. Gear reducer 128 similarly is powered by a power transmission created by belt 134 about gear reducer's 128 pulley 130 and motor's 124 pulley 126.

In operation, pelican 64 is initially in a rest position out of the stream of material. Receiving slot 76 is covered by one or two dust seals 77. When a crosscut sample is to be taken from the stream, air cylinder 58 moves pelican 64 so that receiving slot 76 passes through and beyond the stream. Simultaneously, motor 124 and gear reducer 128 rotate auger 90 at preferably 72 rpm to withdraw all of the sample collected on bottom 78 out through discharge outlet 84. When shaft 60 of air cylinder 58 fully extends, pelican 64 comes to rest under the other dust seal 77 outside of the stream of flowing material. Auger 90 is rotated for a short time longer so that the entire sample material is cleaned out of the pelican 64. In the next sample cycle, shaft 60 is pulled into air cylinder 58 pulling pelican 64 through the stream of material and back to its original rest position. The entire operation may be automated by a switch and relay system or a microprocessor.

The auger 90 cleanout makes this sampler 10 adaptable for any of a multitude of various types of dry material—powder or granular. When sampling grains it may be desirable that motor 124 by explosion proof. The air cylinder 58 driving means to move pelican 64 may be replaced by a motor with chain assembly or a rack and pinion combination. Bottom 78 of pelican 64 may also incline upwards toward discharge elbow 83. A modified sampler 10 may not have housing 10 to sample falling dry material that is not in a vertical duct but may be falling off a conveyor. Additionally, a gear air motor may be used with pulleys 132 and 93 and belt 136 without a gear reducer 128 to form the power transmission.

The present invention may be embodied in other specific forms without departing from the spirit or essential attributes thereof. Therefore, the illustrated embodiments should be considered in all respects as illustrative and not restrictive, reference being made to the appended claims rather than to the foregoing description to indicate the scope of the invention.

That claimed is:

1. A crosscut sampling apparatus for obtaining a representative sample of a downwardly flowing stream of dry material, comprising
   (a) a pelican for catching and holding the sample having a top wall with a receiving slot, a front wall, a bottom for collecting the sample and a discharge outlet in the front wall adjacent the bottom for unloading the sample therethrough from the bottom of the pelican;
   (b) a housing enclosing the pelican and having top and bottom openings for splicing the housing into a gravity feed flow duct containing the downwardly flowing stream of dry material, a side wall and an elongate generally horizontal hole in the side wall in alignment with the discharge outlet for unloading the crosscut sample therethrough from the pelican;
   (c) a support and guide structure for movably mounting the pelican;
   (d) drive means connected to the pelican for moving the pelican along the support structure passing the receiving slot through and beyond the stream to collect the crosscut sample; and
   (e) an auger within the pelican on the bottom adjacent the dischange outlet and rotating means for turning the auger to withdraw the crosscut sample from the bottom of the pelican.

2. The apparatus of claim 1, wherein the front wall of the pelican further comprises an auger tube segment with the auger extending therethrough, the segment being adjacent the bottom of the pelican and extending therefrom through the elongate hole of the housing having the discharge outlet at its end for unloading the crosscut sample from the pelican outside the housing.

3. The apparatus of claim 2, wherein the auger tube segment has a slide panel transversely affixed thereabout adjacent the elongate hole for sliding engagement with the side wall of the housing, the slide panel overlaps the elongate hole in sealing arrangement to prevent exit of the material from the housing through the elongate hole except through the discharge outlet.

4. The apparatus of claim 1, wherein the pelican has a slide panel affixed about the discharge outlet for sliding engagement with the side wall of the housing, the slide panel overlaps the elongate hole in sealing arrangement to prevent exit of the material from the housing through the elongate hole except through the discharge outlet.

5. The apparatus of claim 1, wherein the bottom is concave semi-circular in cross section.

6. The apparatus of claim 1, wherein the front wall and bottom form an angle of at least 90°.

7. A crosscut sampling apparatus for obtaining a representative sample of a downwardly flowing stream of dry material, comprising
   (a) a pelican for catching and holding the sample having a top wall with a receiving slot, a front wall, a bottom for collecting the sample and a discharge outlet in the front wall adjacent the bottom for unloading the sample therethrough from the bottom of the pelican;
   (b) a support and guide structure for movably mounting the pelican comprising stationary tracks and cooperating rollers thereon attached to the pelican for permitting guided movement of the pelican along the tracks through and beyond the stream;
   (c) drive means connected to the pelican for moving the pelican along the support structure passing the receiving slot through and beyond the stream to collect the crosscut sample; and
   (d) an auger within the pelican on the bottom adjacent the discharge outlet and rotating means for turning the auger to withdraw the crosscut sample from the bottom of the pelican.

8. A crosscut sampling apparatus insertable in a gravity feed flow duct containing a downwardly flowing stream of dry material for obtaining a representative crosscut sample of the material, comprising (a) a housing having top and bottom openings for splicing the housing into the duct, a side wall and an elongate generally horizontal hole in the side wall;

(b) a pelican within the housing having a top wall with a receiving slot for permitting the sample material to enter the pelican; front, back, side and bottom walls for containing the sample material, the bottom wall being concave semi-circular in cross section; the front wall having an auger tube segment adjacent the bottom wall extending therefrom through the elongate hole in the housing, the segment having a discharge outlet at its end for unloading therethrough the sample material from the pelican outside the housing;

(c) a support and guide structure for movably mounting the pelican comprising two generally parallel tracks fixed to the housing and cooperating rollers thereon connected to the pelican thereby guiding the receiving slot through and beyond the stream;

(d) a slide panel transversely affixed about the auger tube segment for sliding engagement with the side wall of the housing, the slide panel overlaps the elongate hole in sealing arrangement to prevent exit of the material from the housing through the elongate hole except through the discharge outlet;

(e) drive means connected to the pelican for moving the pelican along the track to thereby move the receiving slot through and beyond the stream of material to collect the crosscut sample; and (f) an auger within the pelican on the bottom wall extending through the auger tube segment to the discharge outlet and rotating means for turning the auger thereby withdrawing the crosscut sample of material from the pelican through the tube segment and out the discharge outlet.

* * * * *